(12) United States Patent
Serebrinsky et al.

(10) Patent No.: US 11,598,704 B2
(45) Date of Patent: Mar. 7, 2023

(54) DEVICE AND METHOD FOR THE DETERMINATION OF ROCK FRACTURE TOUGHNESS OF A RESERVOIR AND THE EFFECT OF CONFINEMENT ON THE FRACTURE TOUGHNESS

(71) Applicants: YPF TECNOLOGÍA S.A., Ciudad Autónoma de Buenos Aires (AR); CONSEJO NACIONAL DE INVESTIGACIONES CIENTÍFICAS Y TÉCNICAS (CONICET), Ciudad Autónoma de Buenos Aires (AR)

(72) Inventors: Santiago Serebrinsky, Ciudad Autónoma de Buenos Aires (AR); Humberto Celleri, Ciudad Autónoma de Buenos Aires (AR); Walter Morris, Ciudad Autónoma de Buenos Aires (AR); Anibal Márquez, Mar del Plata (AR); Juan Belmonte, Mar del Plata (AR)

(73) Assignees: YPF TECNOLOGÍA S.A., Ciudad Autónoma de Buenos Aires (AR); CONSEJO NACIONAL DE INVESTIGACIONES CIENTÍFICAS Y TÉCNICAS (CONICET), Ciudad Autónoma de Buenos Aires (AR)

( * ) Notice: Subject to any disclaimer, the term of this patent is extended or adjusted under 35 U.S.C. 154(b) by 306 days.

(21) Appl. No.: 17/090,198

(22) Filed: Nov. 5, 2020

(65) Prior Publication Data

US 2021/0131932 A1  May 6, 2021

Related U.S. Application Data

(60) Provisional application No. 62/931,367, filed on Nov. 6, 2019, provisional application No. 62/931,025, filed on Nov. 5, 2019.

(51) Int. Cl.
*G01N 3/12* (2006.01)
*G01N 3/06* (2006.01)
*G01N 33/24* (2006.01)

(52) U.S. Cl.
CPC ............... *G01N 3/12* (2013.01); *G01N 3/062* (2013.01); *G01N 33/24* (2013.01);
(Continued)

(58) Field of Classification Search
CPC ... G01N 2203/0019; G01N 2203/0048; G01N 2203/0067; G01N 33/24; G01N 3/12; G01N 3/062
(Continued)

(56) References Cited

U.S. PATENT DOCUMENTS

| 4,075,884 | A | * | 2/1978 | Barker | G01N 3/36 |
| | | | | | 73/807 |
| 4,152,941 | A | * | 5/1979 | Abou-Sayed | G01N 3/12 |
| | | | | | 73/804 |
| 2003/0024323 | A1 | * | 2/2003 | Wang | G01N 3/22 |
| | | | | | 73/847 |

FOREIGN PATENT DOCUMENTS

CN  108303314 A  *  7/2018  ............... G01N 1/28

OTHER PUBLICATIONS

Translation of CN-108303314-A (Year: 2018).*
(Continued)

*Primary Examiner* — Nathaniel T Woodward
(74) *Attorney, Agent, or Firm* — Muncy, Geissler, Olds & Lowe, P.C.

(57) ABSTRACT

A device and method for testing a rock specimen in order to determine the fracture toughness ($K_{IC}$) thereof. The device comprises: a frame; a hydraulic pressure testing rig supported by the frame and comprising a pressure gauge, a lever and a pressure diaphragm; a storage tank for storing hydrau-
(Continued)

lic fluid and supported by the frame; and a pressure chamber supported by the frame, in which the test specimen is placed to be subjected to hydrostatic pressure through conduits that connect said pressure chamber with the storage tank in fluid communication.

20 Claims, 4 Drawing Sheets

(52) U.S. Cl.
CPC ........... *G01N 2203/0019* (2013.01); *G01N 2203/0048* (2013.01); *G01N 2203/0067* (2013.01)

(58) Field of Classification Search
USPC ............................................................ 73/37
See application file for complete search history.

(56) References Cited

OTHER PUBLICATIONS

F. Ouchterlony, "On the Background to the Formulae and Accuracy of Rock Fracture Toughness Measurements using ISRM Standard Core Specimens," Int. J. Rock Meeh. Min. Sci. & Geomech. Abstr. Vol. 26, No. 1, pp. 13-23, 1989, 11 pages.

Finn Ouchterlony, "Fracture Toughness Testing of Rock With Core Based Specimens," Engineering Fracture Mechanics, vol. 35, No. 1/2/3, pp. 351-366, 1991, 16 pages.

Ouchterlony et al., "Suggested Methods for Determining the Fracture Toughness of Rock," International Society for Rock Mechanics, Int. J. Rock Meeh. Min. Sci. & Geomech. Abstr. vol. 25, No. 2, pp. 71-96, 1988, 26 pages.

Serebrinsky et al., "A Method for the Determination of Fracture Toughness in Core Samples Considering Pressure on the Crack Faces," 2018, 9 pages.

Serebrinsky et al., "A Method for the Determination of Fracture Toughness in Core Samples Considering Pressure on the Crack Faces," Instituto Argentine Del Petroleo Y Del Gas, Nov. 9, 2018, Mendoza, Argentina, 21 pages.

Newman, Jr. et al., "Stress Intensity Factor Equations for Cracks in Three-Dimensional Finite bodies Subject to Tension and Bending Loads," NASA Technical Memorandum 85793, Apr. 1984, 41 pages.

Schmidt et al., "Effect of confining pressure on fracture toughness of Indiana limestone," Int. J. Rock Meeh. Min. Sci. Geomech. Abstr., 14, 289-293, 1977, 6 pages.

Al-Shayea et al., "Effects of confining pressure and temperature on mixed-mode (I-II) fracture toughness of a limestone rock," International Journal of Rock Mechanics and Mining Sciences, vol. 37, pp. 629-643, 2000, 15 pages.

M. Thiercelin, "Fracture Toughness and Hydraulic Fracturing," Int. J. Rock Meeh. Min. Sci. Geomech. Abstr., 26, 177-183, 1989, 7 pages.

Thiercelin et al., "Influence of fracture toughness on the geometry of hydraulic fractures," SPE Production Engineering, pp. 435-442, Soc. of Petrol. Eng, 1989, 8 pages.

N. Al-Shayea, "Comparing reservoir and outcrop specimens for mixed mode I-II fracture toughness of a limestone rock formation at various conditions," Rock Meeh. Rock Engng. 35(4), 271-297, 2002, 28 pages.

\* cited by examiner

DEVICE AND METHOD FOR THE DETERMINATION OF ROCK FRACTURE TOUGHNESS OF A RESERVOIR AND THE EFFECT OF CONFINEMENT ON THE FRACTURE TOUGHNESS

CROSS REFERENCE TO RELATED APPLICATIONS

This application claims priority of U.S. Provisional Application No. 62/931,025 filed on Nov. 5, 2019 and U.S. Provisional Application No. 62/931,367 filed on Nov. 6, 2019 under 35 U.S.C. § 119(e), the entire contents of all of which are hereby incorporated by reference.

FIELD OF THE INVENTION

The present invention relates to the field of methods and devices for the determination of mechanical and physical properties. Particularly, the present invention is related to a method and device for the determination of rock fracture toughness of a reservoir and the effect of confinement on said toughness.

BACKGROUND OF THE INVENTION

Shale reservoirs are the most abundant of sedimentary rock types, making up 50% to 80% of sedimentary material worldwide, thus, they are extremely important in a variety of Earth-related topics, including hydrocarbon resources.

The exploration and production of shales steadily increased the quality, quantity and complexity of data used for evaluation and decision making. These considerations allowed for drilling and completion cost reduction, design optimization (e.g., vertical to horizontal wells), productivity enhancement, etc. This improved understanding of shale reservoirs, along with an extensive use of available data, provides a driving force for new experimental methods and associated data analyses.

The successful stimulation of shale reservoirs depends on the availability of important parameters and knowledge on how they affect the outcome of the fracturing treatment and ulterior productivity of drilled wells. The in-situ stress field, pore pressure, fracturing fluid pressure, and the mechanical properties of the rock are of primal importance.

Among the mechanical properties, quantification of the resistance to cracking is needed. From linear elastic fracture mechanics of brittle materials, it is known that the fracture toughness ($K_{IC}$) is one such material property. Fracture toughness is an important parameter influencing hydraulic fracture propagation, in particular for low stress contrasts, low fluid viscosity, and small fractures.

The mechanical properties of a reservoir can be analyzed with different levels of complexity. Fracture properties are generally among the most difficult to determine, and often empirical, qualitative parameters are used to characterize them. Various "brittleness indexes" have been developed for this purpose. However, it is known that these parameters have great limitations to adequately evaluate fracture toughness ($K_{IC}$).

Fracture toughness data on shales are sparse, and they show significant scatter. The microstructure of shales makes material recovery, preservation, and sample manufacture very difficult, while hindering consistent and reproducible experiments. Moreover, fracture toughness is a physically meaningful parameter, as opposed to the phenomenological frackability or brittleness indexes. These indexes are usually regarded as containing limited value, and they often provide opposite conclusions to each other.

It is well known that well conditions (pressure, temperature) have a significant effect on the rock resistance to failure. The combination of these factors leads to the importance of a comprehensive knowledge of fractomechanical behavior (e.g., in terms of fracture toughness) under reservoir and environmental conditions.

U.S. Pat. No. 4,152,941 A, in the name of Terra Tek Inc., describes a method for determining fracture toughness in a rock. The method and device used do not consider the use of controlled temperature.

Consequently, there is a need to provide a device and a method for testing a rock that has low permeability and requires hydraulic stimulation for its exploitation, wherein said test allows obtaining the fracture toughness of the rock in a simple way, as well as the effect of confinement on the toughness. The obtained value of fracture toughness allows to approach the value of fracture toughness under reservoir pressure.

BRIEF DESCRIPTION OF THE INVENTION

The present invention provides a device for testing rock samples and a simple method for determining the fracture toughness of said rock samples, the results of which are capable of being extended to the conditions of a reservoir. In other words, the value determined of fracture toughness by the device and method of the present invention has application in the evaluation of the response of reservoir rock to hydraulic stimulation, which is necessary for shale and/or tight reservoirs.

Therefore, it is an object of the present invention a device for testing a specimen in order to determine the fracture toughness ($K_{IC}$) thereof, wherein said device comprises:
a frame;
a hydraulic pressure testing rig supported by the frame and comprising a pressure gauge, a lever and a pressure diaphragm;
a storage tank for storing hydraulic fluid, supported by the frame; and
a pressure chamber supported by the frame, wherein the test specimen is placed to be subjected to hydrostatic pressure through conduits that connect said pressure chamber with the storage tank in fluid communication.

In an embodiment of the device of the present invention, the specimen is machined from a rock sample.

In a preferred embodiment of the device of the present invention, the rock sample is extracted from an outcrop, from core samples or from reservoir wells.

In an embodiment of the device of the present invention, the pressure chamber comprises hydraulic seals.

In a preferred embodiment of the device of the present invention, the hydraulic seals are O-ring seals.

In an embodiment of the device of the present invention, the hydraulic fluid is water.

In an embodiment of the device of the present invention, the hydraulic fluid is a hydraulic fracture fluid.

In an embodiment of the device of the present invention, the device comprises a displacement gauge for measuring the specimen deformation.

In a preferred embodiment of the device of the present invention, the displacement gauge is a dial indicator.

It is another object of the present invention a method for determining fracture toughness ($K_{IC}$), and the effect of confinement on said fracture toughness, of specimens under controlled conditions, wherein the method comprises the following steps:

preparing the specimens by machining a notch in each one of the specimens;

testing each one of the specimens in a pressure chamber, wherein each test comprises applying hydraulic fluid under controlled pressure to the specimen notch for generating a stress state, and measuring the pressure at which the specimen fractures; and processing the results obtained from the performed tests and calculate the fracture toughness using equation (1):

$$K_{IC} = Y \cdot \sigma \cdot \sqrt{\pi \cdot a} \quad (1)$$

where Y is a shape factor for membrane stresses, a is the notch depth and σ is the applied fluid pressure.

In an embodiment of the method of the present invention, the test is carried out using the device of the present invention.

In a preferred embodiment of the method of the present invention, the method comprises the following steps:

providing a device comprising: a frame; a hydraulic pressure testing rig supported by the frame and comprising a pressure gauge, a lever and a pressure diaphragm; a storage tank for storing hydraulic fluid, supported by the frame; and a pressure chamber supported by the frame, wherein the test specimen is placed to be subjected to hydrostatic pressure through conduits that connect said pressure chamber with the storage tank in fluid communication;

preparing the specimens by machining a notch in each one of the specimens;

testing each one of the specimens in the pressure chamber, wherein each test comprises applying hydraulic fluid under controlled pressure to the specimen notch for generating a stress state, and measuring the pressure at which the specimen fractures; and processing the results obtained from the performed tests and calculate the fracture toughness using equation (1):

$$K_{IC} = Y \cdot \sigma \cdot \sqrt{\pi \cdot a} \quad (1)$$

where Y is a shape factor for membrane stresses, a is the notch depth and σ is the applied fluid pressure.

In an embodiment of the method of the present invention, the specimens are machined from rock samples.

In a preferred embodiment of the method of the present invention, the rock samples are extracted from an outcrop, from core samples or from reservoir wells.

In an embodiment of the method of the present invention, each one of the specimens is machined in a cylindrical shape.

In an embodiment of the method of the present invention, the diameter of each one of the specimens is between 25.4 mm and 45 mm.

In an embodiment of the method of the present invention, the length of each one of the specimens is between 35 mm and 120 mm, preferably between 35 mm and 60 mm.

In an embodiment of the method of the present invention, the notch is machined in a middle portion of each one of the specimens.

In an embodiment of the present method of the invention, the notch is machined with a depth of up to approximately 70% of the specimen diameter, preferably up to 50% of the specimen diameter, more preferably up to 30% of the specimen diameter.

In an embodiment of the method of the present invention, the notch is machined with a radius of the tip of the notch between 0.35 mm and 2 mm.

In a preferred embodiment of the method of the present invention, the shape factor Y is obtained by equation (2):

$$Y = 0.926 - 1.771\left(\frac{a}{D}\right) + 26.421\left(\frac{a}{D}\right)^2 - 78.48\left(\frac{a}{D}\right)^3 + 87.97\left(\frac{a}{D}\right)^4 \quad (2)$$

where D is the diameter of the tested specimen.

DETAILED DESCRIPTION OF THE INVENTION

The present invention provides a device, and a related method of processing the data obtained, for determining fracture toughness in rock samples, and the effect of confining pressure on fracture toughness.

The device for measuring fracture toughness, and the effect of confinement on fracture toughness, together with the method for obtaining these values, according to the present invention, will be described below in detail making reference to FIGS. 1 to 7, which show an embodiment of the device of the present invention and the different elements thereof, an embodiment of the method of the present invention and graphs showing obtained experimental results. Said figures are only examples and should not be considered as limiting.

In each of the figures the same numerical references are used to make reference to same elements of the device of the present invention.

Figure 1:
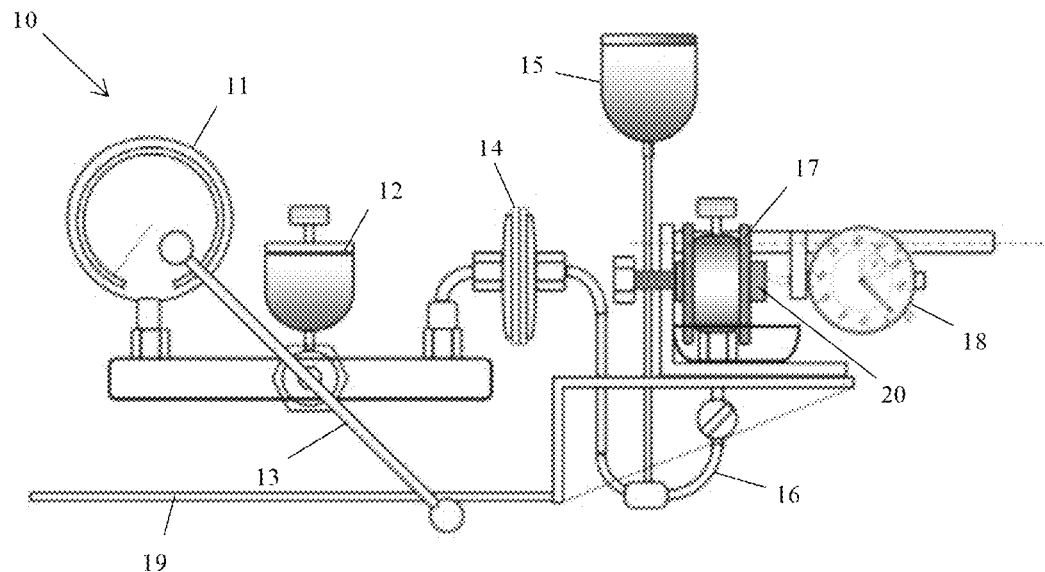
FIG. 1 shows a schematic view of the device of the present invention.

FIG. 1 shows a schematic view of the device 10 of the present invention comprising a pressure gauge 11, a hydraulic pressure testing rig 12, a lever 13, a pressure diaphragm 14, a tank 15 for the storage of hydraulic fluid, conduits 16, a pressure chamber 17, a displacement gauge 18 and a frame 19.

A specimen 20, machined from a rock sample to be tested, is placed in the pressure chamber 17 and is fixed through one of the longitudinal faces thereof to the frame in order to secure its position, whereas in the other face of specimen 20 the displacement gauge 18 is placed, which can be a dial indicator, in order to measure the displacement of the specimen once the hydraulic pressure of the fluid is applied, that is, the deformation the specimen undergoes after being subjected to the hydraulic pressure of the fluid. It is necessary to point out that said displacement gauge is necessary neither to obtain the fracture toughness of the specimen nor to obtain the effect of confinement on said fracture toughness.

The specimen 20 used can be prepared according to the method of the present invention, which will be described below.

The pressure diaphragm 14 separates two parts of the device, one having a hydraulic fluid to be confined within the pressure chamber 17 and the other having hydraulic oil. Turning the lever 13 manually increases the pressure on the hydraulic pressure testing rig 12 and, consequently, on the hydraulic oil. This increase in pressure is visually controlled by the pressure gauge 11, which can be a manometer.

The pressure achieved manually is transmitted to the hydraulic fluid through the pressure diaphragm 14 in such a way that the hydraulic fluid, which arrives from the tank 15 to the pressure chamber 17 and, consequently, to the specimen 20 through the conduits 16, increases its pressure subjecting the specimen 20 and, particularly, a mechanized notch in said specimen 20, to a regulated stress state. In this way, the fracture of the specimen is guaranteed, and conclusions can be drawn from the test performed.

Therefore, device 10 generates, under controlled conditions, a stress state caused by the action of hydraulic fluid confined at the tip of the notch and retrieves information from fracture conditions of the specimens.

Figure 2:
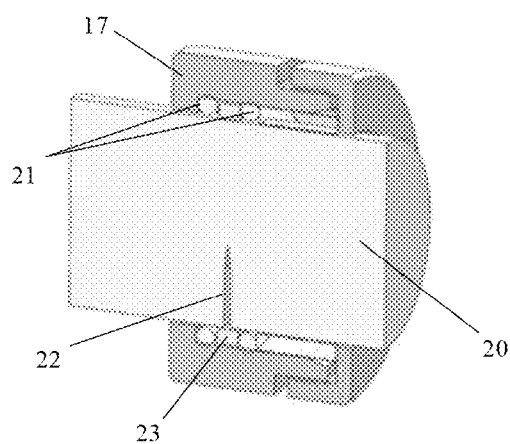
FIG. 2 shows a detailed schematic cross section of the specimen placed in the pressure chamber of the device together with the hydraulic seals.

FIG. 2 shows a detailed schematic cross section of the specimen placed in the pressure chamber 17, where it can be seen the specimen 20, hydraulic seals 21, which can be O-ring seals, a notch 22 and hydraulic fluid 23, which can be water or hydraulic fracture fluid. The hydraulic fluid allows more closely resembling the real conditions of hydraulic fracture in a reservoir.

The hydraulic seals 21 allow to guarantee the fluid tightness of the interior of the pressure chamber 17 in order to confine the hydraulic fluid 23 inside it and put the hydraulic fluid 23 in contact with the specimen 20 and, in particular, with the interior of the notch 22. In this way, a hydraulic fluid 23, when entering under pressure in the notch 22, induces stresses in the faces of the notch 22 causing its opening, that is, the propagation of the notch until the subsequent fracture of the specimen. The recording of burst pressure and the measurement of the notch length allow to calculate the fracture toughness.

The device can be configured to apply remote stress triaxiality to simulate confining pressures and their influence on fracture toughness. This may involve the arrangement of the device within a pressure chamber. Since no mechanical linkage of the confined elements is required for load or displacement measurement, it is also adaptable to high temperature applications.

Figure 3:
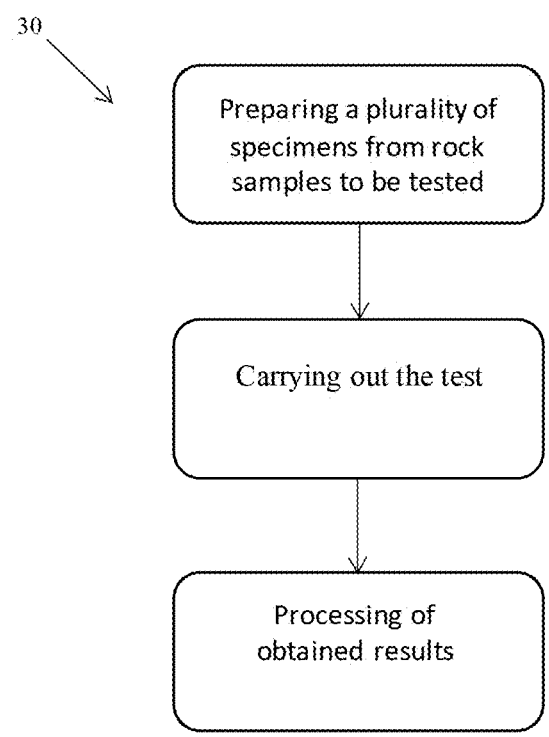
FIG. 3 shows the method of the present invention with the steps thereof.

In FIG. 3 the steps of the method 30 of the present invention can be seen. This method comprises three exemplary steps which should not be considered as limiting the method since said steps could be split into more steps or merged into fewer steps obtaining the same results.

The method 30 of the present invention comprises a step comprising the preparation of mechanized specimens from rock samples to be tested. The rock samples can be extracted from an outcrop located in the vicinity of a reservoir of interest with low permeability, from core samples or directly from the wells of said reservoir, being the last two the preferred options.

The specimens are machined in the form of cylinders with a diameter whose value is between 25.4 mm and 45 mm and a length whose value is between 35 mm and 120 mm, preferably between 35 mm and 60 mm. For example, specimens with a diameter of 38.1 mm and a length of 50.8 mm can be machined. It should be noted that these values are only examples and should not be considered as limiting. Further, all the specimens to be tested can be machined with the same or different diameters.

Next, a notch or crack is machined in each one of the specimens. The notch is machined in a direction perpendicular to the length or longitudinal axis of the specimen. This notch is mechanized in order to weaken the structural integrity of the specimens—as it adds a stress concentrator—and to ensure the breakage of the specimens when applying hydraulic fluid. Also, each notch is machined at its end with a certain radius of the tip of the notch by a suitable cutting tool.

More precisely, a hole is first made by transversely drilling the cylinder that forms the specimen at a desired distance from the external surface of the specimen. In this way, the desired radius of the tip of the notch is obtained, and the desired depth of the notch is established. The cylinder that forms the specimen is then transversely machined, using a cutting tool that is thinner than the diameter of the hole, in order to obtain the notch with the desired depth. The notch depth can be up to approximately 70% of the diameter of the specimen, more preferably up to 50% of the diameter of the specimen, even more preferably up to 30% of the diameter of the specimen, thus having different values in relation to the diameter of the specimen.

Preferably, the notch is machined in a middle portion of the cylinder that each one of the specimens forms, that is, in a central position in relation to the longitudinal axis of each one of the specimens, however, it could also be machined in other positions. In addition, the notch depth (a) on each one of the specimens can be different, so as to obtain equal or different relations between the notch depth and the corresponding specimen diameter.

In a subsequent step of the method of the present invention one of the specimens already machined is placed in the pressure chamber of the device of the present invention and the test is started by applying hydraulic fluid under pressure to the specimen, in particular to the inside of the notch in the specimen. The pressure of the hydraulic fluid is adjustable and shall be measured by the pressure gauge of the device of the present invention. Thus, a stress state is caused, under controlled conditions, by the action of the hydraulic fluid confined to the tip of the notch, and information is retrieved from the fracture conditions of the specimens, as will be seen in the following step.

In a subsequent step of the method of the present invention, the results obtained from the tests performed are processed and different values of fracture toughness are obtained.

It should be noted that the different test methods and sample configurations used to determine the critical stress intensity factor, i.e., fracture toughness $K_{IC}$, typically involve the application of remote loads (tensile, bending, etc.). Given that the initiation and propagation of hydraulic fractures are mainly controlled by the field of in situ stresses, it is possible to achieve similar conditions by applying hydraulic pressure within a notch in a specimen, which causes the propagation and subsequent fracture. Thus, known correlations between the remote load and $K_{IC}$ can be used to determine critical fracture conditions.

Figure 4:
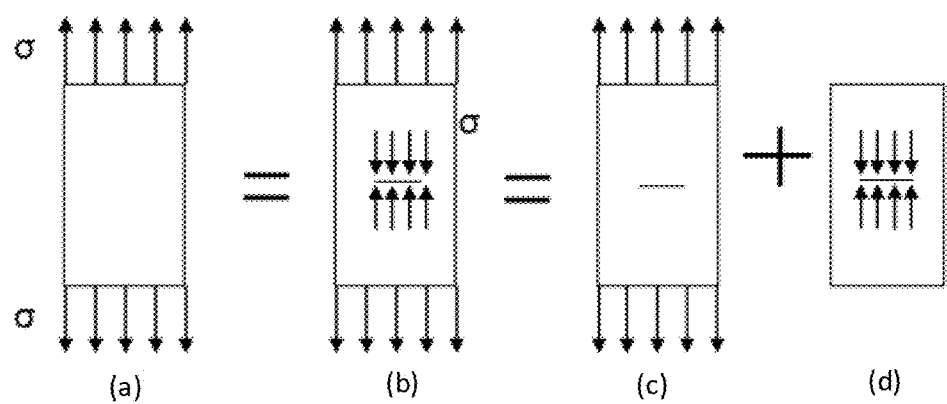
FIG. 4 shows the superposition principle, valid under linear elasticity conditions, applied to the case of a cracked body versus an uncracked body.

The latter is shown in FIG. 4, where $K_{I(a)}$ is zero, there is no crack, which given the superposition principle implies that $K_{I(c)}$ is $-K_{I(d)}$. Consequently, $K_I$ at the tip of the crack subjected to a remote stress state σ is equal to that obtained if the remote stress σ acts on the interior surfaces of that same crack.

In other words, the fractomechanically equivalent system to the remote application of loads is limited to the direct and effective application of pressure on the free surfaces of the crack. This loading condition is similar to the effects of the injection of fracture fluid in the processes of hydraulic fracturing.

Therefore, the goal is to calculate the critical stress intensity factor of rocks $K_{IC}$, derived from the hydraulic fracture pressure of the specimen in the device of the present invention. To that end, $K_{IC}$ is calculated using the shape correction factor proposed in API 579 standard, which explicitly considers the geometry used for the specimens, and considering the superposition principle that equates the case of remote tensile stress applied to the external faces of the cylindrical specimen to the interstitial pressure inside the notch.

Since natural rock generally has a large scatter in properties, even among samples extracted from neighboring material, in order to reduce the uncertainty when performing the test procedure, cementitious material (uniform in constitution, setting time, etc.) is used for calibrating the method.

Unlike metals in general, it is not possible to generate fatigue precrack in a sample by applying controlled fatigue cycles to rocks or cementitious material prior to testing for the determination of $K_{IC}$. Since the actual radius of the tip of the notch may affect the value determined for $K_{IC}$, it is appropriate to evaluate quantitatively this dependence, and to determine the practical limits from which the results converge to a $K_{IC}$ value independent of the geometry.

The value of $K_{IC}$ can be obtained from the burst pressure and according to API 579, appendix C. The analytical solution for the calculation of $K_{IC}$ considers a zero crack width (planar defect):

$$K_{IC} = (M_m \cdot \sigma_m + M_b \cdot \sigma_b)\sqrt{\pi \cdot a} \quad (3)$$

where $M_m$ and $M_b$ are shape factors for the membrane and bending stresses, respectively, in the section. Under the test conditions of the method, $\sigma_m$ is the applied fluid pressure and $\sigma_b$ is zero, since there are no bending stresses applied. Since $\sigma_b$ is zero, it is not necessary to calculate the coefficient $M_b$. The shape factor $M_m$ is $$M_m = 0.926 - 1.771\left(\frac{a}{D}\right) + 26.421\left(\frac{a}{D}\right)^2 - 78.48\left(\frac{a}{D}\right)^3 + 87.97\left(\frac{a}{D}\right)^4$$

where a is the notch depth and D is the diameter of the tested specimen.

Given the test conditions of the method, equation (3) can be rewritten to be equivalent to equation (1), which was previously presented:

$$K_{IC} = Y \cdot \sigma \cdot \sqrt{\pi \cdot a} \quad (1)$$

where σ is a stress equal to $\sigma_m$ and Y is a shape factor equal to $M_m$.

Experimental Results

Cement specimens with a diameter of $D_0 = 37.6$ mm were machined. These specimens were notched with variable notch depths (a), between 4 mm and 14 mm, and with radii of the tip of the notch (r) of 0.5 mm, 1 mm and 1.5 mm. The 0.5 mm radius was obtained by a sawing technique. The radii of the tip of the notch of 1 mm and 1.5 mm were obtained by cross drilling with a drill bit up to the distance required by the pre-set notch length, and subsequent sawing of the remaining ligament. Said specimens were placed in the device of the present invention and tested.

Figure 5:
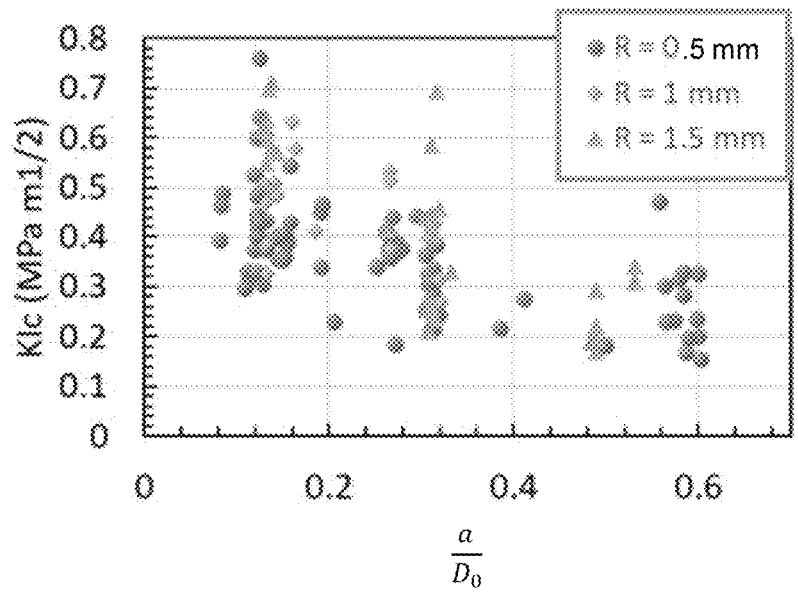
FIG. 5 shows the $K_{IC}$ results obtained for cement specimens with different relations between notch depth and specimen diameter and with different values of the radius of the tip of the notch.

In FIG. 5, a graph showing the results of these tests can be seen. In particular, it can be seen the different values adopted by the fracture toughness ($K_{IC}$) for different values of radius of the tip of the notch and relations between the notch depth and the diameter of the tested specimens.

It is evident from the results of FIG. 5 that there is a clear dependence between the notch depth and the fracture toughness, for the different radii.

For non-zero radii, the obtained value may not be representative of the fractomechanic property, but can be used comparatively among different materials, if the notch is standardized.

The dependency of the values of fracture toughness with the geometry of the notch may stem from at least three factors: a) the non-zero thickness of the notch, since shape factors are defined for planar defects (without separation between fracture faces); b) notch bottom with non-zero actual radius, and c) the possible effect of radial compression on the material confined between the seals of the pressure chamber.

Factors a) and b) can be included in the fracture toughness formulation by appropriately modifying the shape factor Y, according to the actual geometry. This correction can be made by determining the value of $K_{IC}$ by finite elements simulations.

The remaining divergence, after applying the corrected shape factor, will depend on other variables such as the eventual dependence of $K_{IC}$ on the hydrostatic component of the stress state generated in the sample.

The device and method of the present invention are easily adaptable to the study of the effect of variable hydraulic loads, which are considered important to analyze the action of the fluids and proppants against partial closure of cracks. In addition, the effect of reservoir conditions (pressure, temperature) on $K_{IC}$, often considered of primal relevance in the outcome of the stimulation treatment, could be incorporated with suitable cells.

Figure 6:
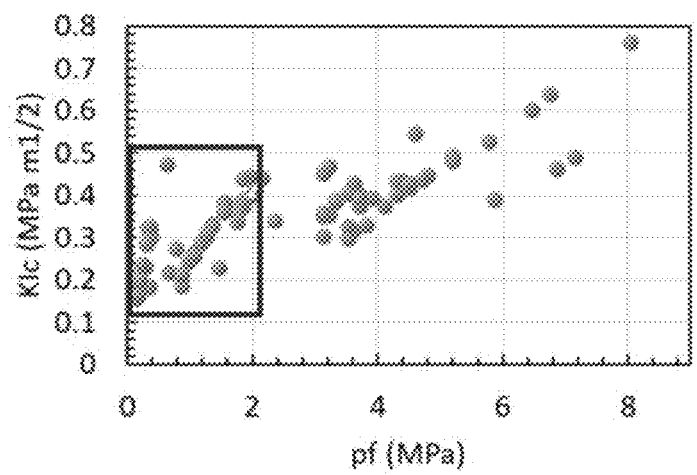
FIGS. 6 and 7 show the $K_{IC}$ results obtained for cement specimens in relation to the confining pressure.
Figure 7:
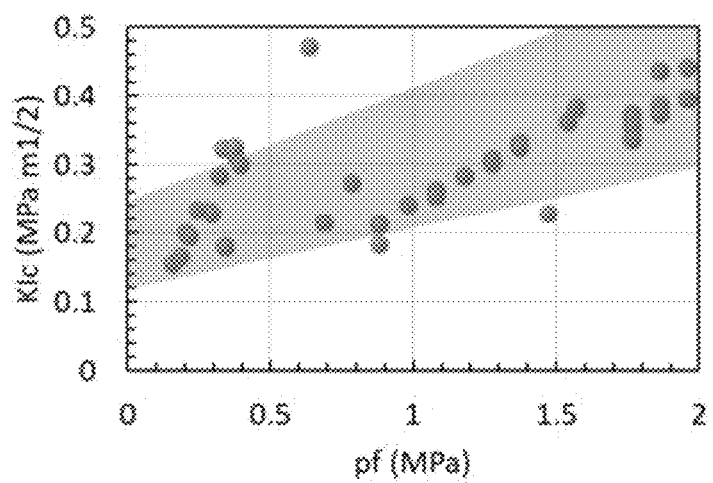

Finally, the effect of confining pressure on the specimen and, in particular, on fracture toughness, can be analyzed. It is important to determine this effect because the rocks in a reservoir are also confined to the pressures thereof. To determine this effect, the values of fracture toughness $K_{IC}$, obtained in the graph of FIG. 5, are plotted as a function of the failure pressure, which was the pressure required to cause the fracture of each of the specimens. This failure pressure is in turn the confining pressure ($p_f$) to which the external surface of the specimen and the notch are subjected. FIG. 6 shows the relationship between confining pressure and fracture toughness. FIG. 7 shows an enlarged view of the box shown in FIG. 6. It can be seen from the results shown in FIGS. 6 and 7 that fracture toughness increases with confining pressure. In particular, from the results obtained, an adjustment can be made through a straight line, wherein the equation of said straight line:

$$K_{IC} = 0.21 \text{ MPa}\sqrt{m} + 0.080\sqrt{m} \cdot p_f$$

where 0.080 is the slope of the straight line and the coefficient of increase in fracture toughness.

It should be clarified that, although the experimental tests were obtained from cement specimens, these tests can be carried out using specimens from rock samples.

The invention claimed is:

1. A device for testing a specimen in order to determine the fracture toughness ($K_{IC}$) thereof, wherein said device comprises:
   a frame;
   a hydraulic pressure testing rig supported by the frame and comprising a pressure gauge, a lever and a pressure diaphragm;
   a storage tank for storing hydraulic fluid, supported by the frame; and
   a pressure chamber supported by the frame, wherein the test specimen is placed to be subjected to hydrostatic pressure through conduits that connect said pressure chamber with the storage tank in fluid communication.

2. The device according to claim 1, wherein the pressure chamber comprises hydraulic seals.

3. The device according to claim 2, wherein the hydraulic seals are O-ring seals.

4. The device according to claim 1, wherein the hydraulic fluid is water.

5. The device according to claim 1, wherein the hydraulic fluid is a hydraulic fracture fluid.

6. The device according to claim 1, wherein the device comprises a displacement gauge for measuring the specimen deformation.

7. The device according to claim 6, wherein the displacement gauge is a dial indicator.

8. A method for determining fracture toughness ($K_{IC}$), and the effect of confinement on said fracture toughness, of specimens under controlled conditions, wherein the method comprises the following steps:
   providing a device comprising a frame; a hydraulic pressure testing rig supported by the frame and comprising a pressure gauge, a lever and a pressure diaphragm; a storage tank for storing hydraulic fluid, supported by the frame; and a pressure chamber supported by the frame, wherein the test specimen is placed to be subjected to hydrostatic pressure through conduits that connect said pressure chamber with the storage tank in fluid communication;
   preparing the specimens by machining a notch in each one of the specimens;
   testing each one of the specimens in the pressure chamber, wherein each test comprises applying hydraulic fluid under controlled pressure to the specimen notch for generating a stress state, and measuring the pressure at which the specimen fractures; and
   processing the results obtained from the performed tests and calculate the fracture toughness using equation (1):

$$K_{IC} = Y \cdot \sigma \cdot \sqrt{\pi \cdot a} \qquad (1)$$

where Y is a shape factor for membrane stresses, a is the notch depth and σ is the applied fluid pressure.

9. The method according to claim 8, wherein the specimens are machined from rock samples.

10. The method according to claim 9, wherein the rock samples are extracted from an outcrop, from core samples or from reservoir wells.

11. The method according to claim 8, wherein each one of the specimens is machined in a cylindrical shape.

12. The method according to claim 8, wherein the diameter of each one of the specimens is between 25.4 mm and 45 mm.

13. The method according to claim 8, wherein the length of each one of the specimens is between 35 mm and 120 mm.

14. The method according to claim 13, wherein the length of each one of the specimens is between 35 mm and 60 mm.

15. The method according to claim 8, wherein the notch is machined in a middle portion of each one of the specimens.

16. The method according to claim 8, wherein the notch is machined with a depth of up to approximately 70% of the specimen diameter.

17. The method according to claim 16, wherein the notch is machined with a depth of up to 50% of the specimen diameter.

18. The method according to claim 17, wherein the notch is machined with a depth of up to 30% of the specimen diameter.

19. The method according to claim 8, wherein the notch is machined with a radius of the tip of the notch between 0.35 min and 2 mm.

20. The method according to claim 8, wherein the shape factor Y is obtained by equation (2):

$$Y = 0.926 - 1.771\left(\frac{a}{D}\right) + 26.421\left(\frac{a}{D}\right)^2 - 78.48\left(\frac{a}{D}\right)^3 + 87.97\left(\frac{a}{D}\right)^4 \qquad (2)$$

where D is the diameter of the tested specimen.

* * * * *